(12) United States Patent
Molenda et al.

(10) Patent No.: US 7,744,656 B2
(45) Date of Patent: *Jun. 29, 2010

(54) COLOURING COMPOSITION

(75) Inventors: Michael Molenda, Frankfurt (DE); Martin Hoffmann, Zwingenberg (DE); Mustafa Grit, Gernsheim (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/186,351

(22) Filed: Aug. 5, 2008

(65) Prior Publication Data

US 2009/0038086 A1  Feb. 12, 2009

(30) Foreign Application Priority Data

Aug. 7, 2007 (EP) .................................. 07015548

(51) Int. Cl.
*A61Q 5/10* (2006.01)
(52) U.S. Cl. ........................ 8/405; 8/435; 8/552; 8/581; 8/638; 8/644
(58) Field of Classification Search ................ 8/405, 8/435, 552, 581, 638, 644, 654
See application file for complete search history.

(56) References Cited

U.S. PATENT DOCUMENTS 6,540,791 B1 * 4/2003 Dias .............................. 8/111

2004/0103488 A1   6/2004 Yamashita
2004/0197284 A1 * 10/2004 Auguste ................... 424/70.12
2005/0226838 A1 * 10/2005 Krause et al. ............. 424/70.13
2005/0244442 A1 * 11/2005 Sabino et al. ................ 424/401

FOREIGN PATENT DOCUMENTS

| DE | 202004014826 U1 | 2/2005 |
|----|---|---|
| EP | 1398022 A | 3/2004 |
| EP | 1464324 A | 10/2004 |
| EP | 1543820 A | 6/2005 |
| EP | 1787634 A | 5/2007 |
| JP | 07089844 A | 4/1995 |
| WO | 9531173 A | 11/1995 |

OTHER PUBLICATIONS

M.D. Berthiaume: "Silicones in Hair Fixatives and Finishing Products" Drug and Cosmetic Industry, May 1995.
English Language Abstract for EP 1464324, (2004).
English Language Abstract for DE 202004014826, (2005).
English Language Abstract for JP 089844, (1995).

* cited by examiner

*Primary Examiner*—Eisa B Elhilo
(74) *Attorney, Agent, or Firm*—Norris, McLaughlin & Marcus

(57) ABSTRACT

The present invention is related to an aqueous colouring composition for keratin fibers especially human hair based on hair direct dyes and optionally oxidative dyes and comprising at least one arylated silicone.

17 Claims, No Drawings

COLOURING COMPOSITION

The present invention is related to an aqueous colouring composition for keratin fibres especially human hair.

Hair colouring has been widely practiced for ages. The colorations are divided into two main groups, the first being permanent colouration based on mainly oxidative hair dyes which penetrate into hair and polymerize, and the second is based on direct dyes which is, without excluding any penetration, mainly adsorbed onto hair and widely based on cationic and neutral dyes. In the latter, recently compositions based on anionic direct dyes have also been made available by the applicant which deliver brilliant, shiny and long lasting colours.

In hair colouration, one of the purposes is certainly change the hair colour and/or cover any inhomogeneous hair colours in particular grey hair. Another purpose is to refresh shine, brilliance and vibrancy of hair colour. Especially in hair shine wide variability has been observed and there is, therefore, need for further improvements.

The present invention starts with the above mentioned problem of hair shine after hair colouration either with direct dyes.

The inventors of the present invention have surprisingly found out that a composition comprising at least one direct dye and at least one arylated silicone colours hair excellently and improves hair shine, vibrancy and brilliance excellently. In addition the compositions of the present invention conditions hair in terms of combability, elasticity, smoothness and softness.

Accordingly, the subject of the present invention is an aqueous hair colouring composition comprising at least one direct dye and at least one arylated silicone.

Another subject of the present invention is use of composition comprising at least one direct dye and at least one arylated silicone for enhancing shine, brilliance and vibrancy of keratin fibres especially hair.

The compositions of the present invention comprises at least one arylated silicone at a concentration range of 0.01 to 5%, preferably 0.05 to 4% more preferably 0.1 to 3% and most preferably 0.1 to 2.5% by weight calculated to total composition prior to mixing with oxidizing lotion. Non-limiting suitable examples are diphenyl dimethicone, diphenylsiloxy phenyl trimethicone, tetramethyl tetraphenyl trisiloxane, triphenyl trimethicone, tetramethly tetraphenyl trisiloxane and trimethyl pentaphenyl trisiloxane.

In the preferred embodiment of the present invention, the arylated silicone comprises at least 2 phenyl groups, more preferably 3 and most preferably 4, and in particular 5 phenyl groups in its molecule.

Preferred arylated silicones are tetramethyl tetraphenyl trisiloxane, triphenyl trimethicone, tetramethly tetraphenyl trisiloxane and trimethyl pentaphenyl trisiloxane.

More preferred are tetramethyl tetraphenyl trisiloxane, tetramethly tetraphenyl trisiloxane and trimethyl pentaphenyl trisiloxane.

Particularly preferred arylated silicone is trimethyl pentaphenyl trisiloxane available from Dow Corning under the trade name DC PH-1555 HRI.

It should be noted that compositions of the present invention can also comprise more than one arylated silicone.

All concentration mentioned within the description refers to the concentration of the respective compound in the composition prior to mixing with any other composition, if necessary, unless otherwise mentioned.

Composition of the present invention comprises at least one direct dye. Direct dyes suitable within the meaning of the present invention are anionic, cationic and neutral nitro dyes. Plant dyes can also be used within the compositions of the present invention.

In principal any direct dye suitable for colouring keratin fibres especially hair is useful within the scope of the present invention.

One category of the suitable direct dyes is cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. In other words, cationic, anionic and nitro dyes are used in mixture within the meaning of the present invention. When using direct dyes of various categories, their compatibility must be taken into account.

Among the direct dyes cationic and nitro dyes are preferred ones. Most preferred ones are cationic direct dyes.

Concentration of direct dyes in the compositions of the present invention is within the range of 0.001 to 5%, preferably 0.01 to 4% and more preferably 0.05 to 3%, and most preferably 0.1 to 2% by weight, calculated to total composition.

In a further embodiment of the present invention, compositions comprise at least one oxidative hair dye precursor (developing substance).

As a rule, it is possible to incorporate any developing substances known per se. Special mention is made of p-phenlynediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxyethyl)amino-benzene, 2-(2-hydroxyethyl amino)-5-amino-toluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxypyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture of each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total composition, whereby these figures are always related to the proportion of free base.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl) aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hydroxyethylamino) benzene, 1-amino-3-[bis(2'-hydroxy-ethyl)amino]benzene, α-naphthol, 4,6-dichlororesorcinol, 1,3-diamino-toluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total composition, whereby these figures always relate to the proportion of free base.

Further, Indole and indoline derivatives can as well be contained in the colouring composition of the present invention. Examples to those are: 6-aminoindol, 6-hydroxyindole, 1-ethyl-6-hydroxyindole, 1-methyl-4-hydroxyindol, 1-methyl-6-hydroxyindole, 2-methyl-6-hydroxyindole, 5-hydroxyindol, 4-hydroxyindol, 5,6-dihydroxyindole, 6-aminoindoline, 6-hydroxyindoline, 1-ethyl-6-hydroxyindoline, 1-methyl-4-hydroxyindoline, 1-methyl-6-hydroxyindoline, 2-methyl-6-hydroxyindoline, 5-hydroxyindoline, 4-hydroxyindoline, 5,6-dihydroxyindoline and their respective salts.

In further embodiment of the present invention, compositions comprise mixtures of the hair dyes mentioned above. In other words, a hair dyeing composition comprises at least one direct dye and at least one oxidative dye precursor, optionally at least one coupling substance. Direct dyes are here as well selected from cationic, anionic and nitro dyes. Above mentioned concentration for each class of dyestuff are also valid here.

Colouring compositions according to the present invention can be in the form of emulsion, solution, dispersion, thickened liquid and/or gel. Emulsion form is preferred.

With the term thickened liquid, it is meant that the compositions comprise additionally a thickening agent.

With the term gel it is meant that the compositions comprise additionally a gelling agent and the gelling agent is a polymer forming a shear thinning gel.

The thickening agents include any polymer either natural or synthetic thickening aqueous composition. Examples are cellulose and its derivatives such as hydroxyethylcellulose, guar and its derivatives such as hydroxypropyl guar. In the selection of the thickening agent compatibility with any other components of the formulation should carefully be examined.

The gelling agents include polymers either synthetic or natural forming shear thinning compositions. Examples to the natural polymers are xanthan gum and its derivatives. Synthetic shear thinning polymers may be those of acrylate polymers commercially available for example under trade name Carbopol. In the selection of the geling agent compatibility with any other components of the formulation should carefully be examined.

It should be noted that gelling and thickening agents can also be used in mixture. Concentration of the thickening and/or gelling agents should be in the range of 0.05 to 5%, preferably 0.1 to 2.5% by weight calculated to total content.

Compositions of the present invention further comprise at least one surfactant selected from non-ionic, cationic, anionic and amphoteric ones and their mixtures. Preferred surfactants are non-ionic, cationic and amphoteric ones and their mixtures. Most preferred are non-ionic and cationic surfactants and their mixtures.

As a rule any cationic surfactant is suitable for the compositions of the present invention. With the term cationic surfactant it is meant that the surfactant carries a cationic charge when used in the compositions. In other words, compounds having no cationic charge but when added into the compositions protonate and therewith become cationic are also included within the definition of cationic surfactant. An example to such may be stearyldimethylamine and PEG-2 Cocamine are as a compound not carrying a cationic charge but when used in a composition having acidic pH becomes cationic by protonation.

Preferably at least one cationic surfactant is selected from the compounds with the general formula

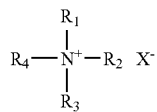

where $R_1$ s a saturated or unsaturated, branched or non-branched alkyl chain with 8-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_2$ is a hydrogen, saturated or unsaturated, branched or non-branched alkyl chain with 1-22 C atoms or

where $R_5$ is saturated or unsaturated, branched or non-branched alkyl chain with 7-21 C atoms and n has typical value of 0-4 or

where $R_6$ is saturated or unsaturated, branched or non-branched alkyl chain with 7-21 C atoms and n has typical value of 0-4, and $R_3$ and $R_4$ are independent from each other H or lower alkyl chain with 1 to 4 carbon atoms or ethoxy or propoxy group with number of ethoxy or propoxy groups varying in the range of 0 to 4, and X is chloride, bromide or methosulfate.

Suitable cationic surfactants are, for example, long-chain quaternary ammonium compounds which can be used alone or in admixture with one another, such as cetyl trimethyl ammonium chloride, myristoyl trimethyl ammonium chloride, behentrimonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, stearamidopropyldimethylamoonium chloride, dipalmitoyl dimonium chloride, distearyl dimethyl ammonium chloride, stearamidopropyl trimonuim chloride.

Further examples to the cationic surfactants are so called esterquats available on the market, for example, under the trade names "Schercoquat®", "Dehyquart®L80" and "Tetranyl®". Still further examples are so called amidoquats again available on the market, for example, under the trade name "INCROQUAT$^a$ HO" or "OCS".

Suitable non-ionic surfactants are alkyl polyglucosides of the general formula

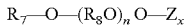

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 50, preferably about 10 and about 30.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant suitable for the compositions according to the present invention are amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate.

Further surfactants suitable within the meaning of the present invention are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_9-(C_2H_4O)_n-O-CH_2COOX,$$

wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Further suitable anionic surfactants are also $C_8$-$C_{22}$-acyl aminocarboxylic acids or the water-soluble salts thereof, such as N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Total surfactant concentration varies between 0.1 and 15%, preferably 0.5 and 10%, and more preferably 1 to 7.5% by weight calculated to total composition.

Compositions of the present invention can be in the form of emulsion especially oil in water (O/W) emulsion. Emulsions according to the present invention preferably comprise at least one fatty alcohol with linear of branched alkyl chain. Suitable ones are fatty alcohols having 12 to 22 C atoms in its alkyl chain. Examples are myristyl alcohol, cetyl alcohol, stearyl alcohol, behenyl alcohol and their mixtures. Preferred are cetyl, stearyl and behenyl alcohol and their mixtures i.e. cetearyl alcohol. Fatty alcohols may be included into the compositions of the present invention at a concentration of 0.1 to 20%, preferably 0.5 to 15% and more preferably 1 to 10% by weight calculated to total composition.

Emulsions should also comprise at least one emulsifier. Suitable emulsifiers are those surfactants mentioned above. Preferred emulsifiers are non-ionic, cationic and anionic surfactant mentioned above. Among the non-ionic surfactant fatty alcohol ethoxylates are the most proffered ones. Among cationic surfactants any cationic surfactant with a single alkyl chain is suitable. Sulfate types of anionic surfactants are the preferred anionic surfactants. The above mentioned concentrations are also suitable for the emulsifiers mentioned here.

Colouring composition of present invention can comprise additionally fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition. Fatty acid examples, without limiting the choice, suitable for colouring compositions are myristic acid, palmitic acid, behenic acid, stearic acid, oleic acid, linoleic acid. The most preferred fatty acid is oleic acid.

Compositions of the present invention can comprise additionally hair conditioning compounds such as oils, cationic polymers, non-ionic substances. Oils as conditioners according to the present invention are selected from silicone oils either volatile or non-volatile, natural and synthetic oils. Among silicone oils those can be added to the compositions include either volatile or non-volatile dimethicone, dimethiconol, polydimethylsiloxane, DC fluid ranges from Dow Corning, cyclosiloxanes such as DC 245, arylated silicones such as phenyltrimethicone available from Dow Corning under trade name DC 556. Synthetic oils include mineral oil such as paraffin oil and petrolatum.

Natural oils suitable are such as olive oil, almond oil, avocado oil, ricinus oil, coconut oil, palm oil, sesame oil, peanut oil, whale oil, sunflower oil, peach kernel oil, wheat germ oil, macadamia nut oil, night primrose oil, jojoba oil, castor oil, or soya oil, lanolin and the derivatives thereof.

Lipophilic oily compounds such as fatty acid esters are also suitable for the composition of the present invention. Examples are such as isopropyl myristate, palmitate, stearate and isostearate, oleyl oleate, isocetyl stearate, hexyl laurate, dibutyl adipate, dioctyl adipate, myristyl myristate, oleyl erucate, cetyl palmitate, etc.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_9 CO (OCH_2CH_2)_n OH$$

$$R_9 CO (OCH_2CH_2)_n O OC R_{10}$$

where $R_9$ and $R_{10}$ are independent from each other saturated, unsaturated or branched or non-branched alkyl chain with 7 to 21 C atoms and n is typically 2-100.

Composition of the present invention can comprises cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has especially been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46, Polyquaternium 67.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

Further cationic polymers are so called aminated silicones such as amodimethicone. The cationic polymers also include the quaternized products of graft polymers from organopolysiloxanes and polyethyl oxazolines described in EP-A 524 612 and EP-A 640 643.

Concentration range for any of the additional conditioners mentioned above is in the range of 0.01 to 10% by weight, preferably 0.05-7.5% by weight, more preferably 0.1-5% by weight calculated to the total composition.

The compositions according to the present invention can also comprise further agents, such as protein hydrolyzates and polypeptides, e.g. keratin hydrolyzates, collagen hydrolyzates of the type "Nutrilan" or elastin hydrolyzates, as well as, in particular vegetable, optionally cationized protein hydrolyzates, for example "Gluadin".

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, green tea, blue lotus flower, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapone" products and "Herbasol$^R$". Extracts and the preparation thereof are also described in "Hagers Handbuch der pharmazeutischen Praxis", $4^{th}$ Ed.

The compositions can contain one or more organic solvents such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvent can be in the range of 1 to 40%, preferably 1 to 25% by weight, calculated to total composition.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2.2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total composition.

The compositions of the present invention can comprise one or more hair-restructuring agents. The hair restructuring agents preferred are especially the ones disclosed in the German patent DE 197 51 550 C2. Namely they are ceramide type of compounds, fatty acids and phytosterol or their mixtures.

Preferred ceramide compound is cetyl-PG-hydroxyethylpalmitamide.

Preferred fatty acids are those with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

The concentration of ceramide in the compositions of the present invention can be in the range of 0.01 to 2% and especially 0.01 to 1% by weight calculated to the total weight of the composition. The fatty acids may be contained at a level of 0.01 to 2.5% and especially 0.01 to 1% by weight calculated to the total weight of the composition. Phytosterol concentration of the conditioners is less than 1% and preferably in the range of 0.01 to 0.5% by weight calculated to the total weight of the composition. It should be noted without limiting the use of those ingredients the effect of those hair restructuring ingredients is especially elevated when used in combination with penetration enhancers.

Furthermore, compositions of the present invention can comprise particulate matter dispersed in it such as synthetic mica. Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference.

Suitable metal oxide or oxides for coating synthetic mica are titanium dioxide, chromium oxide, ferric oxide or mixtures thereof. In the present invention the preferred is synthetic mica coated with titanium dioxide. Such materials are commercially available from Sun Chemical Corporation and are known with their INCI names Synthetic Fluorphologopite.

The particle size distribution of synthetic mica coated with a metal oxide or oxides is in the range of 1 to 750 µm, preferably 1 to 250 µm, more preferably 1 to 100 µm and most preferably 20 to 95 µm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition.

The pH of the compositions according to the invention is in the range of 2 to 11. in the preferred embodiment of the present invention, pH of the compositions comprising only direct dyes and used without mixing with an oxidizing agent is in the range of 2 to 7, preferably 2.5 to 6, more preferably 3 to 5. On the other hand, when a composition is mixed with an oxidizing agent independent from its content in terms of dyestuffs, preferred pH range is between 5 to 11, preferably 6 to 11, more preferably 6.8 to 10. pH of the compositions can be adjusted by using any organic and/or inorganic acids and alkalizing agents such as ammonium hydroxide and monoethanolamine or their mixtures.

Composition of the present invention can be used as it is in case those only direct dyes are contained or after mixing with an oxidizing agent. In case that the compositions of the present invention is mixed with an oxidizing composition prior to application onto hair, lightening (highlighting) and colouring is achieved at the same time. The oxidizing agents suitable are hydrogen peroxide, urea peroxide, melamin peroxide or perborate salts. The most preferred is hydrogen peroxide, which is used as a lotion containing 2 to 12% by weight, calculated to composition only comprising hydrogen peroxide.

The new composition as a result of mixing colouring and oxidizing composition allows achieving simultaneous lightening and coloring. The mixing ratio of the colouring composition and oxidizing composition should be in the range of 4:1 to 1:4, by weight, preferably 2:1 to 1:3 by weight.

Colouring and highlighting with compositions of the present invention can be carried out in several different ways.

One of the processes is that colouring composition of the present invention is mixed with an oxidizing composition and applied onto hair and after a processing time of 5 to 45 min at a temperature of 20 to 45° C. and rinsed off from hair.

Another way of carrying out highlighting and colouring is that of two step application. In the first step, composition comprising at least one oxidizing agent is applied onto hair and left on the hair for 5 to 45 min and without rinsing off, the colouring agent is applied onto hair in the second step and after processing additional 5 to 45 min the mixed compositions are rinsed of from hair.

In the above mentioned two step colouring and highlighting process, between the application of first and second agents, the hair can be washed with water and optionally hair can be dried.

In the lightening and colouring process using the colouring composition of the present invention, the lightening can as well be carried out with a composition known as bleaching agents. For such a process suitable bleaching composition is for example the one disclosed in a European Patent No 560 088. Preferred way of carrying out lightening an colouring using bleaching agents is two step process as mentioned above wherein a bleaching composition comprising at least one bleaching agent is mixed with an oxidizing agent and applied onto hair, after processing time of 5 to 45 min rinsed off from hair and colouring composition of the present invention is applied and after processing tome of 5 to 45 min rinsed off from hair.

Furthermore, compositions of the present invention can comprise all substances customarily found in such preparations. Examples of such substances are complexing agents, preservatives, fragrances, and antioxidants such as sodium sulfit.

Following examples are to illustrate the invention but not to limit.

EXAMPLE 1

|  | % by weight |
| --- | --- |
| Basic red 51 | 0.2 |
| Trimethyl pentaphenyl trisiloxane | 0.5 |
| Hydroxyethyl cellulose | 1.0 |
| Citric acid/Sodium hydroxide | q.s. to pH 4.0 |
| Fragrance, preservative | q.s. |
| Water | to 100 |

The above composition was prepared by dissolving cationic dye any hydroxyethyl cellulose in water and subsequently dispersing trimethyl pentaphenyl trisiloxane which was followed by adding further substances and adjusting the pH.

The above composition delivered intensive shiny red colour on medium blonde hair. Excluding pentaphenyl trimethly trisiloxane resulted in loss of shine. The composition was mixed to homogeneity prior to application, if any tendency to separate was observed.

EXAMPLE 2

|  | % by weight |
| --- | --- |
| Cetearyl alcohol | 10.0 |
| Behentrimonium chloride | 2.0 |
| Trimethyl pentaphenyl trisiloxane | 0.8 |
| Basic red 51 | 0.2 |
| Citric acid/Sodium hydroxide | q.s. to pH 4.0 |
| Fragrance, preservative | q.s. |
| Water | to 100 |

Above composition was prepared first by emulsifying cetearyl alcohol, behentrimonium chloride and Trimethyl pentaphenyl trisiloxane at a temperature of approximately 75° C. in part of water. Afterwards the composition was cooled down and Basic red 51 dissolved in part of water was added. Finally, remaining water, preservative and fragrance was added and pH was adjusted.

For comparative purposes the same composition but not comprising pentaphenyl trimethly trisiloxane was also produced.

The above composition was tested in a half side test against the comparative composition without pentaphenyl trimethly trisiloxane with 10 volunteers having shoulder length hair. Comments from the volunteers were both side felt soft and combable but the side treated with the inventive composition had significantly more shine, brilliance and vibrancy than the side treated with the comparative composition. The preference was 9/1.

EXAMPLE 3

|  | % by weight |
| --- | --- |
| Cetearyl alcohol | 10.0 |
| Behentrimonium chloride | 2.0 |
| Trimethyl pentaphenyl trisiloxane | 1.0 |
| Basic red 51 | 0.2 |
| Monoethanolamine | q.s. to pH 10.0 |
| Fragrance, preservative | q.s. |
| Water | to 100 |

The composition was prepared in the same way as in example 2.

For comparative purposes the same composition but not comprising Trimethyl pentaphenyl trisiloxane was also produced.

The above composition was tested in a half side test against the comparative composition without Trimethyl pentaphenyl trisiloxane with 10 volunteers having shoulder length hair. The above composition was mixed with a composition comprising 9% hydrogen peroxide at a weight ratio of 1 to 1 and applied onto hair streaks and processed for 30 min at a temperature of 40° C. and rinsed off. Comments from the volunteers were streaks on both side felt soft and combable but the streaks obtained with the inventive composition has significantly more shine, brilliance and vibrancy than the side treated with the comparative composition. The preference was 9/1.

EXAMPLE 4

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Trimethyl pentaphenyl trisiloxane | 1.0 |
| Basic red 51 | 0.5 |
| Ammonium hydroxide | q.s. to pH 10.0 |
| Fragrance, preservative | q.s. |
| Water | to 100 |

Similar results were observed with the above composition as in Example 3.

EXAMPLE 5

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Trimethyl pentaphenyl trisiloxane | 0.5 |
| Diphenyl dimethicone | 0.5 |
| Basic red 51 | 0.5 |
| Acid red 52 | 0.5 |
| Ammonium hydroxide | q.s. to pH 10.0 |
| Fragrance, preservative | q.s. |
| Water | to 100 |

Similar results were observed with the above composition as in Example 3.

EXAMPLE 6

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Trimethyl pentaphenyl trisiloxane | 0.5 |
| Dimethicone | 0.5 |
| Basic red 51 | 0.5 |
| HC Red 3 | 0.5 |
| Ammonium hydroxide | q.s. to pH 10.0 |
| Fragrance, preservative | q.s. |
| Water | to 100 |

Similar results were observed with the above composition as in Example 3.

EXAMPLE 7

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Trimethyl pentaphenyl trisiloxane | 1.0 |
| Basic red 51 | 0.05 |
| 2,5,6-Triamino-4-hydroxypyrimidinsulfat | 0.01 |
| 2,5-Diaminotoluolsulfat | 0.55 |
| 4-Chlorresorcin | 0.17 |
| Resorcin | 0.05 |
| 3-Aminophenol | 0.03 |
| Sodium sulfite | 1.0 |
| Citric acid/Sodium hydroxide | q.s. to pH 10.0 |
| Fragrance, preservative | q.s. |
| Water | to 100 |

For comparative purposes the same composition but not comprising Trimethyl pentaphenyl trisiloxane was also produced.

The above composition was tested in a half side test against the comparative composition without Trimethyl pentaphenyl trisiloxane with 10 consumers having shoulder length hair. The above composition was mixed with a composition comprising 6% hydrogen peroxide at a weight ratio of 1 to 1 and applied onto hair and processed for 30 min at a temperature of 40° C. and rinsed off. Comments from the consumer were that both side felt soft and combable but the colour achieved with the inventive composition had significantly more shine, brilliance and vibrancy than the side treated with the comparative composition. 8 volunteers preferred the side according to the invention and 2 could not see any difference.

EXAMPLE 8

|  | % by weight |
| --- | --- |
| Cetearyl alcohol | 10.0 |
| Cocamide MEA | 4.0 |
| Sodium lauryl sulphate | 1.5 |
| Propylene glycol | 2.0 |
| Trimethyl pentaphenyl trisiloxane | 1.0 |
| 2,5,6-Triamino-4-hydroxypyrimidinsulfat | 1.05 |
| 4-amino-hydroxytoluol | 0.55 |
| Basic red 51 | 0.10 |
| Acid red 52 | 0.05 |
| Sodium sulfite | 1.0 |
| Monoethanolamine | q.s. to pH 10.0 |
| Fragrance, preservative | q.s. |
| Water | to 100 |

Similar results were observed as in example 7.

EXAMPLE 9

|  | % by weight |
| --- | --- |
| Cetearyl alcohol | 10.0 |
| Cocamide MEA | 4.0 |

-continued

| | % by weight |
|---|---|
| Sodium lauryl sulphate | 1.5 |
| Propylene glycol | 2.0 |
| Trimethyl pentaphenyl trisiloxane | 0.8 |
| Phenyl trimethicone | 0.1 |
| 2,5,6-Triamino-4-hydroxypyrimidinsulfat | 0.02 |
| 2,5-Diaminotoluolsulfate | 0.43 |
| HC Yellow 5 | 0.10 |
| 4-amino hydroxytoluol | 0.02 |
| Resorcin | 0.10 |
| m-aminophenol | 0.07 |
| Sodium sulfite | 1.0 |
| Monoethanolamine | q.s. to pH 10.0 |
| Fragrance, preservative | q.s. |
| Water | to 100 |

Similar results were observed as in Example 7.

EXAMPLE 10

In this example, hair was bleached first with a bleaching composition according to EP 560 088 B1 according to the method as disclosed in the description of the patent and bleaching composition was rinsed off from hair. In the second step composition according to Example 4 as given above was applied onto hair without mixing with oxidizing composition. Hair streaks obtained showed excellent shiny, brilliant and vibrant intensive red colour.

EXAMPLE 11

| | % by weight |
|---|---|
| Cetearyl alcohol | 10.0 |
| Behentrimonium chloride | 2.0 |
| Trimethyl pentaphenyl trisiloxane | 0.3 |
| Basic red 76 | 0.1 |
| Basic red 51 | 0.1 |
| Citric acid/Sodium hydroxide | q.s. to pH 4.0 |
| Fragrance, preservative | q.s. |
| Water | to 100 |

EXAMPLE 12

| | % by weight |
|---|---|
| Cetearyl alcohol | 10.0 |
| Cocamide MEA | 4.0 |
| Sodium lauryl sulphate | 1.5 |
| Propylene glycol | 2.0 |
| Trimethyl pentaphenyl trisiloxane | 1.0 |
| Basic red 51 | 0.5 |
| Acid red 52 | 0.5 |
| Lactic acid | q.s. to pH 3.5 |
| Fragrance, preservative | q.s. |
| Water | to 100 |

EXAMPLE 13

| | % by weight |
|---|---|
| Acid red 52 | 1.0 |
| Propylene carbonate | 25.0 |
| Ethanol | 5.5 |
| Xanthan gum | 1.0 |
| Trimethyl pentaphenyl trisiloxane | 0.3 |
| Lactic acid | q.s. to pH 2.5 |
| Fragrance, preservative | q.s. |
| Water | to 100 |

EXAMPLE 14

| | % by weight |
|---|---|
| Basic orange 31 | 0.05 |
| Basic yellow | 0.2 |
| Guar gum | 1.0 |
| Trimethyl pentaphenyl trisiloxane | 0.1 |
| Diphenyl dimethicone | 0.3 |
| Lactic acid | q.s. to pH 4.5 |
| Fragrance, preservative | q.s. |
| Water | to 100 |

EXAMPLE 15

| | % by weight |
|---|---|
| Cetearyl alcohol | 10.0 |
| Cetrimonium chloride | 1.0 |
| Polyquaternium-10 | 0.5 |
| Trimethyl pentaphenyl trisiloxane | 1.0 |
| Basic red 51 | 0.2 |
| Lactic acid/sodium hydroxide | q.s. to pH 4.0 |
| Fragrance, preservative | q.s. |
| Water | to 100 |

EXAMPLE 16

| | % by weight |
|---|---|
| Cetearyl alcohol | 10.0 |
| Cetrimonium chloride | 1.0 |
| Polyquaternium-10 | 0.5 |
| Trimethyl pentaphenyl trisiloxane | 1.0 |
| Basic red 51 | 0.2 |
| Benzophenone-3 | 0.2 |
| Lactic acid/sodium hydroxide | q.s. to pH 4.0 |
| Fragrance, preservative | q.s. |
| Water | to 100 |

EXAMPLE 17

| | % by weight |
|---|---|
| Cetearyl alcohol | 10.0 |
| Ceteareth-20 | 3.0 |
| Cetrimonium chloride | 0.5 |
| Polyquaternium-10 | 0.75 |
| Trimethyl pentaphenyl trisiloxane | 1.0 |
| Basic red 51 | 0.2 |
| Benzophenone-3 | 0.2 |
| Lactic acid/sodium hydroxide | q.s. to pH 3.5 |
| Fragrance, preservative | q.s. |
| Water | to 100 |

EXAMPLE 18

| | % by weight |
|---|---|
| Cetearyl alcohol | 10.0 |
| Ceteareth-20 | 3.0 |
| Cetrimonium chloride | 0.5 |
| Polyquaternium-10 | 0.5 |
| Amodimethicone | 0.5 |
| Trimethyl pentaphenyl trisiloxane | 0.2 |
| Synthetic fluorphologopite* | 1.0 |
| Basic red 51 | 0.2 |
| Benzophenone-3 | 0.2 |
| Lactic acid/sodium hydroxide | q.s. to pH 3.5 |
| Fragrance, preservative | q.s. |
| Water | to 100 |

*Synthetic fluorphologopite used is commercially available from Sun Chemical Corporation under the trade name SunShine Glitter White with a particle size distribution in the range of 20 to 95 μm.

EXAMPLE 19

| | % by weight |
|---|---|
| Cetearyl alcohol | 10.0 |
| Ceteareth-20 | 3.0 |
| Cetrimonium chloride | 0.5 |
| Polyquaternium-10 | 0.5 |
| Polysilicone-9 | 0.5 |
| Trimethyl pentaphenyl trisiloxane | 0.5 |
| Basic red 51 | 0.2 |
| Benzophenone-3 | 0.2 |
| Lactic acid/sodium hydroxide | q.s. to pH 4.0 |
| Fragrance, preservative | q.s. |
| Water | to 100 |

EXAMPLE 20

| | % by weight |
|---|---|
| Cetearyl alcohol | 10.0 |
| Cocamide MEA | 4.0 |
| Sodium lauryl sulphate | 1.5 |
| Propylene glycol | 2.0 |
| Amodimethicone | 0.5 |
| Trimethyl pentaphenyl trisiloxane | 0.8 |

-continued

| | % by weight |
|---|---|
| 2,5,6-Triamino-4-hydroxypyrimidinsulfat | 0.01 |
| 2,5-Diaminotoluolsulfat | 0.55 |
| 4-Chlorresorcin | 0.17 |
| Resorcin | 0.05 |
| 3-Aminophenol | 0.03 |
| HC Yellow 5 | 0.08 |
| Sodium sulfite | 1.0 |
| Citric acid/Sodium hydroxide | q.s. to pH 10.0 |
| Fragrance, preservative | q.s. |
| Water | to 100 |

The invention claimed is:

1. An aqueous composition for colouring keratin fibres especially human hair comprising at least one direct dye selected from the group consisting of cationic, anionic and neutral nitro dyes and at least one arylated silicone selected from the group consisting of diphenylsiloxy phenyl trimethicone, tetramethyl tetraphenyl trisiloxane, triphenyl trimethicone, and tetramethyl tetraphenyl trisiloxane.

2. The aqueous composition according to claim 1, wherein the direct dye is present at a concentration of 0.001 to 5% calculated to total composition.

3. The aqueous composition according to claim 1 comprising at least two arylated silicones.

4. The aqueous composition according to claim 1 wherein the arylated silicone is present at a concentration of 0.01 to 5% by weight calculated to total composition.

5. The aqueous composition according to claim 1 further comprising at least one surfactant selected from the group consisting of non-ionic, cationic, anionic and amphoteric surfactants.

6. The aqueous composition according to claim 1 further comprising at least one conditioning agent.

7. The aqueous composition according to claim 1 further comprising at least one oxidative dye precursor.

8. The aqueous composition according to claim 1 further comprising at least one oxidizing agent.

9. The aqueous composition according to claim 1 wherein the composition has a pH between 2 and 11.

10. A process for colouring hair wherein a composition according to claim 1 is applied onto hair and rinsed off from hair after a processing time of 5 to 45 min at a temperature of 20 to 45° C.

11. A process for colouring hair wherein a composition according to claim 1 is mixed first with a composition comprising at least one oxidizing agent and applied onto hair and rinsed off from hair after a processing time of 5 to 45 min at a temperature of 20 to 45° C.

12. A process for colouring hair wherein hair is bleached with a bleaching composition and after rinsing bleaching agent from hair a composition according to claim 1 is applied onto hair and rinsed off from hair after a processing time of 5 to 45 min at a temperature of 20 to 45° C.

13. A process for colouring and highlighting hair wherein a composition comprising at least one oxidizing agent is applied onto hair and left on the hair for 5 to 45 min and without rinsing off, the colouring agent according to claim 1 is applied onto hair in the second step and after processing additional 5 to 45 min the mixture is rinsed of from hair.

14. The aqueous composition according to claim 1 further comprising at least one fatty alcohol.

15. The aqueous composition according to claim 1 further comprising at least one organic solvent.

16. The aqueous composition according to claim 1 further comprising at least one UV filter.

17. The aqueous composition according to claim 7 further comprising at least one coupling agent.

* * * * *